(12) United States Patent
Huizenga et al.

(10) Patent No.: US 10,266,470 B2
(45) Date of Patent: Apr. 23, 2019

(54) PROCESS FOR THE SEPARATION OF GLYCOLS

(71) Applicant: SHELL OIL COMPANY, Houston, TX (US)

(72) Inventors: Pieter Huizenga, Amsterdam (NL); Kai Jürgen Fischer, Amsterdam (NL); Karin Bus, Amsterdam (NL); Waldo Eugene De Villiers, Katy, TX (US); Carmelo Perez Golf, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 4 days.

(21) Appl. No.: 15/564,438

(22) PCT Filed: Apr. 5, 2016

(86) PCT No.: PCT/EP2016/057387
§ 371 (c)(1),
(2) Date: Oct. 5, 2017

(87) PCT Pub. No.: WO2016/162316
PCT Pub. Date: Oct. 13, 2016

(65) Prior Publication Data
US 2018/0079702 A1    Mar. 22, 2018

(30) Foreign Application Priority Data

Apr. 7, 2015 (EP) .................................... 15162619

(51) Int. Cl.
*C07C 29/82* (2006.01)
*C07C 29/80* (2006.01)
*C07C 31/20* (2006.01)

(52) U.S. Cl.
CPC .............. *C07C 29/82* (2013.01); *C07C 29/80* (2013.01)

(58) Field of Classification Search
CPC ........ C07C 29/80; C07C 29/82; C07C 31/202
See application file for complete search history.

(56) References Cited

U.S. PATENT DOCUMENTS

| 4,966,658 A | 10/1990 | Berg |
| 5,423,955 A | 6/1995 | Berg |
| 2011/0312050 A1 | 12/2011 | Zhang et al. |

FOREIGN PATENT DOCUMENTS

| CN | 102643165 A | 8/2012 |
| CN | 103772148 A | 5/2014 |

(Continued)

OTHER PUBLICATIONS

International Search Report and Written Opinion received for PCT Patent Application No. PCT/EP2016/057387, dated Jul. 18, 2016, 8 pages.

*Primary Examiner* — Brian A McCaig

(57) ABSTRACT

The invention provides a process for the separation of MEG and 1,2-BDO from a first mixture comprising MEG and 1,2-BDO in a weight ratio of at least 10:1 (MEG:1,2-BDO), said process comprising the steps of; (i) providing the first mixture as a feed to a distillation column at a point in the range of from 20 to 80% of the column height; (ii) operating the distillation at a temperature in the range of from 120 to 190° C. and at a pressure in the range of from 5 kPa to atmospheric pressure; (iii) removing an MEG stream from the distillation column at a point below the point at which the first mixture is fed; (iv) removing an overheads stream comprising an azeotrope of MEG and 1,2-BDO.

8 Claims, 4 Drawing Sheets

(56) References Cited

FOREIGN PATENT DOCUMENTS

EP             3126315 A1     2/2017
WO     WO 2015/150520 A1 * 10/2015  ............. C07C 29/82

* cited by examiner

PROCESS FOR THE SEPARATION OF GLYCOLS

PRIORITY CLAIM

The present application is the National Stage (§ 371) of International Application No. PCT/EP2016/057387, filed Apr. 5, 2016, which claims priority from European Patent Application No. 15162619.9, filed Apr. 7, 2015 incorporated herein by reference.

FIELD OF THE INVENTION

The present invention relates to a process for the selective separation of glycols.

BACKGROUND OF THE INVENTION

Ethylene glycol and propylene glycol are valuable materials with a multitude of commercial applications, e.g. as heat transfer media, antifreeze, and precursors to polymers, such as PET. Ethylene and propylene glycols are typically made on an industrial scale by hydrolysis of the corresponding alkylene oxides, which are the oxidation products of ethylene and propylene, produced from fossil fuels.

In recent years, increased efforts have focused on producing chemicals, including glycols, from renewable feedstocks, such as sugar-based materials. For example, US 2011/312050 describes a continuous process for the catalytic generation of polyols from cellulose, in which the cellulose is contacted with hydrogen, water and a catalyst to generate an effluent stream comprising at least one polyol.

CN 102643165 is directed to a catalytic process for reacting sugar in an aqueous solution with hydrogen in the presence of a catalyst in order to generate polyols.

As with many chemical processes, the reaction product stream in these reactions comprises a number of desired materials, diluents, by-products and other undesirable materials. In order to provide a high value process, the desirable product or products must be obtainable from the reaction product stream in high purity with a high percentage recovery of each product and with as low as possible use of energy and complex equipment.

In known processes to make glycols, the glycols are usually present at high dilution in a solvent, typically water. The water is usually removed from the glycols by distillation. Subsequent purification of the glycols is then carried out by fractional distillation. This process can have high costs both in terms of capital and operational expenditure. Further, repeated heating or maintenance at raised temperatures in the distillation steps may also lead to decomposition of the desired glycol products.

When glycols are produced by hydrogenolysis of sugars, a mixture of glycols is produced. The main glycol constituents in the reaction product stream are monoethylene glycol (MEG), monopropylene glycol (MPG) and 1,2-butanediol (1,2-BDO). The separation of these glycols by fractional distillation is complicated due to the similarity in boiling points, particularly between MEG and 1,2-BDO (respectively 198 and 196.8° C.). Further, the isolation of a pure MEG overheads stream by fractional distillation from a mixture comprising MEG and 1,2-BDO is made impossible by the formation of a homogeneous minimum boiling azeotrope between MEG and 1,2-BDO at atmospheric pressure. Degradation of the products at high temperatures prevents higher than atmospheric pressure being used for distillation.

U.S. Pat. No. 4,966,658 is directed to the separation of a mixture of 1,2-BDO and MEG using a process known as azeotropic distillation in which an azeotrope-forming agent is added to the mixture before distillation in order to facilitate separation. A similar process is described in U.S. Pat. No. 5,423,955 for the separation of 1,2-BDO and MPG. Azeotropic distillation can lead to an increase in relative volatility between the components but also leads to further process steps in order to remove the azeotrope forming agents.

CN103772148 describes an azeotropic distillation process using an extraction agent for separating MEG and 1,2-butanediol.

Co-pending application EP 14163242.2 discloses a process for separating monoethylene glycol from a mixture comprising monoethylene glycol and 1,2-butanediol, using a two column, pressure-swing distillation set-up.

It would be advantageous to provide a simple and efficient method suitable for the recovery of MEG from a mixture comprising MEG and 1,2-BDO.

SUMMARY OF THE INVENTION

Accordingly, the present invention provides a process for the separation of MEG and 1,2-BDO from a first mixture comprising MEG and 1,2-BDO in a weight ratio of at least 10:1 (MEG:1,2-BDO), said process comprising the steps of:
(i) providing the first mixture as a feed to a distillation column at a point in the range of from 20 to 80% of the column height;
(ii) operating the distillation at a temperature in the range of from 120 to 190° C. and at a pressure in the range of from 5 kPa to atmospheric pressure;
(iii) removing an MEG stream from the distillation column at a point below the point at which the first mixture is fed;
(iv) removing an overheads stream comprising an azeotrope of MEG and 1,2-BDO.

DETAILED DESCRIPTION OF THE INVENTION

Figure 1:
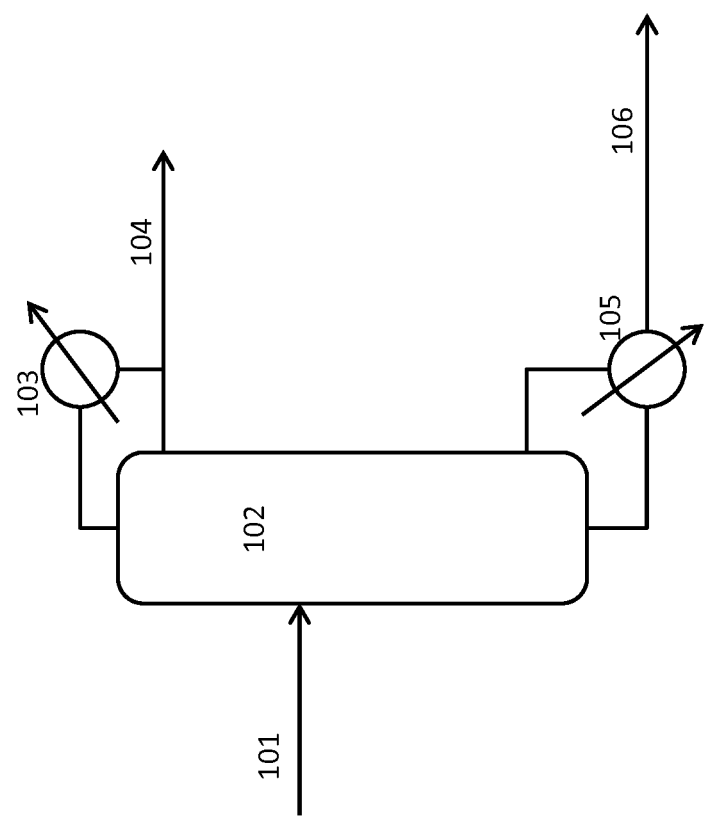
FIGS. 1 to 3 are schematic diagrams of exemplary, but non-limiting, embodiments of a process for the separation of glycols as described herein.

The present inventors have found that MEG can be effectively separated with high recovery and excellent MEG product purity from a mixture comprising MEG and 1,2-BDO in a weight ratio of at least 10:1 (MEG:1,2-BDO) by using a single distillation column wherein an azeotrope of a small amount of the MEG present with the 1,2-BDO is removed as an overhead stream. In a preferred embodiment, further MEG may be recovered by further processing steps of the small MEG, 1,2-BDO azeotrope stream.

The process may be applied to any mixture comprising MEG and 1,2-BDO in a ratio of MEG:1,2-BDO of at least 10:1. Preferably, the first mixture comprising MEG and 1,2-BDO is derived from the reaction product stream from a process for the production of glycols. In a particularly preferred embodiment of the invention, the first mixture comprising MEG and 1,2-BDO is derived from the reaction product stream from a process for the hydrogenolysis of a saccharide or sugar alcohol containing feedstock.

Typically, the reaction product stream from a process for the hydrogenolysis of a saccharide or sugar alcohol containing feedstock comprises, as glycols, at least MEG, MPG and 1,2-BDO. These glycols are typically present at a concentration in the range of from 0.1 to 30 wt % of the overall stream.

In such a reaction product stream, MEG is suitably present as at least 10 wt %, preferably as at least 20 wt %, more preferably at least 30 wt % of the non-solvent fraction of the stream. MEG is suitably present as at most 95 wt %, preferably.

In such a reaction product stream, MPG is suitably present as at least 2 wt %, preferably as at least 4 wt % of the non-solvent fraction of the stream. MPG is suitably present as at most 60 wt %, preferably as at most 45 wt % of the non-solvent fraction of the stream.

In such a reaction product stream, 1,2-BDO is suitably present as at least 1 wt %, preferably as at least 2 wt % of the non-solvent fraction of the stream. 1,2-BDO is suitably present as at most 20 wt %, preferably as at most 4 wt % of the non-solvent fraction of the stream.

As well as the glycols, the reaction product streams from hydrogenolysis reactions of saccharides or sugar alcohols may comprise solvent (particularly water), oxygenates, hydrocarbons, catalyst, degradation products, and gases in any composition. The variety of compounds and their concentration depend on the saccharide or sugar alcohol containing feedstock and the various hydrogenation and hydrogenolysis conversion conditions, including catalysts, reaction conditions such as temperature, pressure and saccharide or sugar alcohol concentration. However, suitably the hydrogenolysis reactions have gone to completion and the aqueous stream contains less than 5 wt %, preferably less than 2 wt %, more preferably less than 1 wt %, even more preferably less than 0.5 wt %, most preferably substantially no saccharides or sugar alcohols when considered as a weight percentage of the overall stream. Typically, the aqueous stream also contains less than 5 wt %, preferably less than 2 wt %, more preferably less than 1 wt %, even more preferably less than 0.5 wt %, most preferably substantially no glycerol, when considered as a weight percentage of the overall stream.

If the first mixture comprising MEG and 1,2-BDO is derived from such a reaction product stream, one or more treatment, separation and/or purification steps may be applied to the reaction product stream before the process of the present invention. Such steps may include one or more of: removal of at least a portion of the solvent present, for example by distillation; removal of light ends; fractional distillation to produce a glycols stream and removal of heavy organics and any inorganics present, such as catalyst material; and initial separation steps to achieve preliminary separation of glycols, e.g. separation of MPG by fractional distillation or other distillation process that results in a stream in which essentially all of the glycols remaining are MEG and 1,2-BDO.

The first mixture comprising MEG and 1,2-BDO has a weight ratio of MEG:1,2-BDO of at least 10:1. Preferably, the weight ratio of MEG:1,2-BDO is as high as possible. In certain embodiments a weight ratio of MEG:1,2-BDO of at least 30:1 may be used.

The first mixture is provided as a feed to a distillation column. Any suitable distillation column may be used, including packed columns and columns provided with trays). The number of theoretical stages required for this separation is in the range of 50 to 80 theoretical stages.

The distillation is carried out at a temperature in the range of from 120° C. to 190° C. and at a pressure in the range of from 5 kPa to atmospheric pressure. Standard atmospheric pressure is considered to be 101.325 kPa, although this will vary depending on locality and local conditions. In one preferred embodiment, the distillation is carried out at a temperature in the range of from 175 to 185° C. and close to atmospheric pressure.

An overheads stream comprising an azeotrope of MEG and 1,2-BDO is removed from the distillation column as an overheads stream. The overheads stream preferably contains in the range of from 30 to 55 wt % MEG, depending on the pressure at which the column is operated.

In a preferred embodiment of the invention, the azeotrope of MEG and 1,2-BDO may be subjected to further process steps in order to recover the MEG and, optionally, the 1,2-BDO. Such steps may include a pressure-swing distillation such as that described in co-pending application EP 14163242.2. Alternatively an azeotropic distillation with a suitable entrainer may be carried out. Applying an extra process to this stream can result in increased recovery of MEG, without the high cost involved in applying such a process to the entire stream.

An MEG stream is removed from the distillation column at a point below the point at which the first mixture is fed. In one embodiment, the MEG stream is removed from the distillation column as a bottoms stream. In this embodiment, heavy ends may be present in the bottoms stream with the MEG. Alternatively, the MEG stream may be removed from the distillation column at a point below the point at which the first mixture is fed and above the bottoms stream. In this embodiment, the bottoms stream will mainly comprise heavy ends.

Suitably, the MEG stream removed from the distillation column at a point below the point at which the first mixture is fed will contain in the range of from 99 to 99.99 wt % MEG. The amount will depend on heavies content. In the embodiment wherein MEG is removed as a bottoms stream and heavy ends are present with the MEG, said heavy ends may be removed via a separate distillation column in order to provide an enriched MEG stream. Optionally, the MEG stream may be subjected to further processing steps to further increase its purity, as required. Suitably, the MEG stream will contain at least 80 wt % of the MEG in the first mixture comprising MEG and 1,2-BDO provided to the distillation column. Preferably, the MEG stream will contain at least 90 wt %, more preferably at least 95 wt %, even more preferably at least 98 wt %, of the MEG in the first mixture comprising MEG and 1,2-BDO provided to the distillation column at least. Such an amount is referred to as the MEG recovery.

Figure 2:
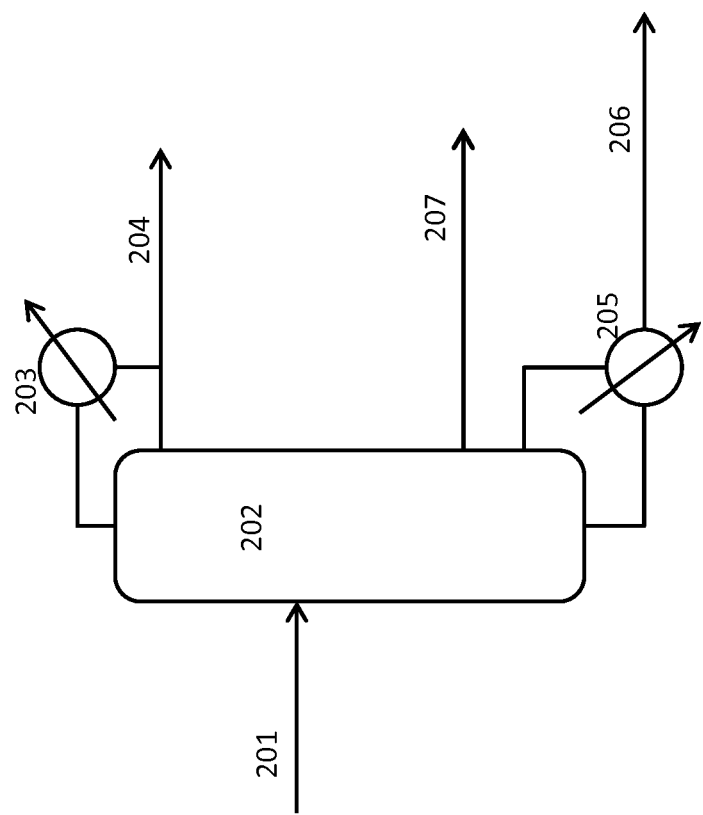
Figure 3:
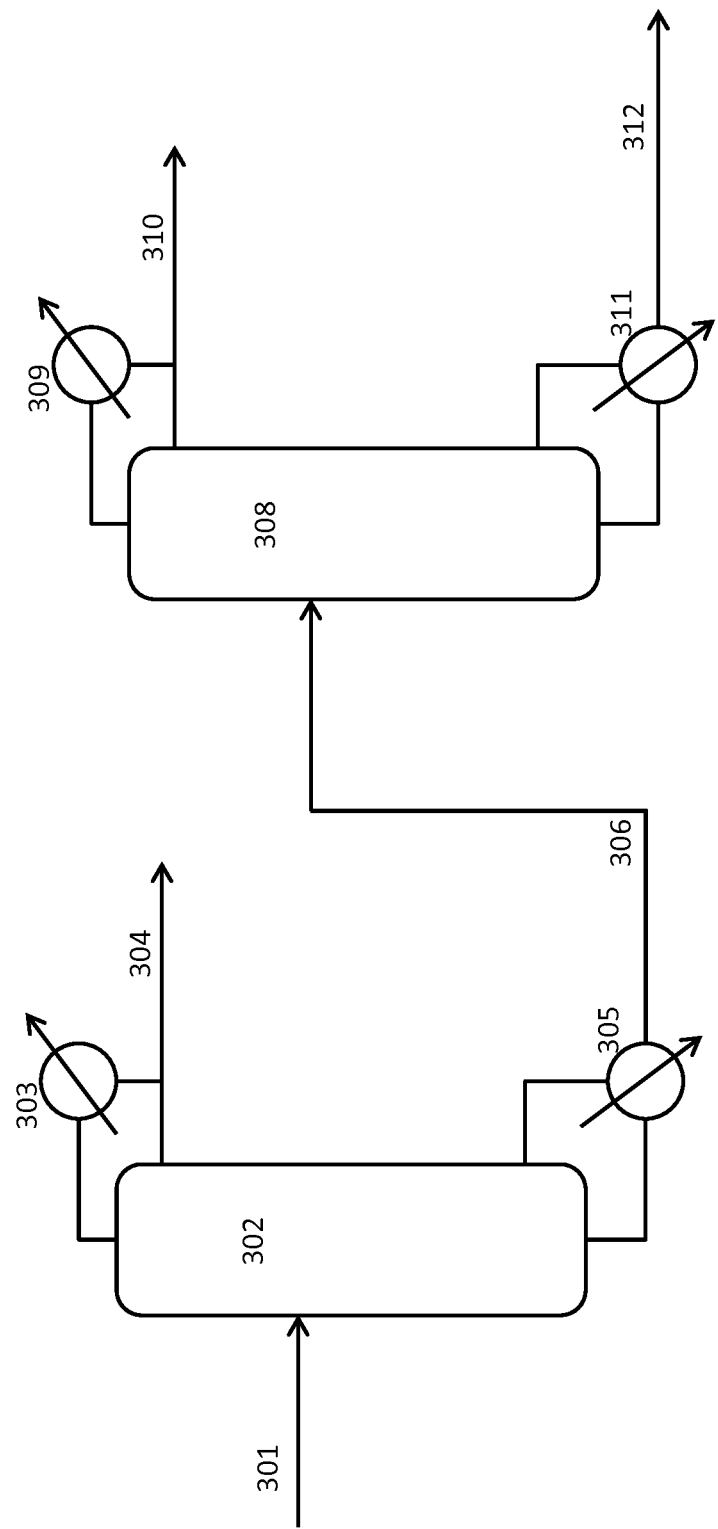

The present invention is further illustrated in the preferred, but non-limiting, embodiments of the invention illustrated in FIGS. 1 to 3. In these Figures, the first digit of each reference number refers to the Figure number (i.e. 1XX for FIG. 1 and 2XX for FIG. 2). The remaining digits refer to the individual features and the same features are provided with the same number in each Figure. Therefore, the same feature is numbered 104 in FIG. 1 and 204 in FIG. 2.

In FIG. 1, a first mixture comprising MEG and 1,2-BDO 101 is provided to a distillation column 102 equipped with a reboiler 105 and a condenser 103. The overheads stream provides an azeotrope of MEG and 1,2-BDO 104. The bottoms stream 106 is the MEG stream.

In the alternative embodiment shown in FIG. 2, the bottoms stream 206 contains heavy ends and a separate MEG stream 207 is removed at a point below the point at which the first mixture is fed and above the bottoms stream.

FIG. 3 shows the embodiment illustrated in FIG. 1 with further treatment of the MEG stream 306 in a separate distillation column 308 providing an enriched MEG stream 310 as overheads and heavy ends as the bottoms stream 312.

EXAMPLES

Aspen Plus software was used to model the process. A thermodynamic package was used. Said package resulted from fitting of the experimental basic data (VLE) measured for the mixtures considered.

Examples were run with the following MEG/12-BDO ratio: 40:1, 20:1, 10:1, 80:1, with no heavies present. Another example was run with a MEG/1,2-BDO ratio of 40:1 with heavies present in the feed. The results are shown in Tables 1 to 7, below.

TABLE 1

MEG/1,2-BDO Ratio of 40; 95% MEG Recovery

|  | Feed | Top | Bottom |
|---|---|---|---|
| Temperature | 170° C. | 175° C. | 180° C. |
| Pressure | 0.6 Bar | 0.5 Bar | 0.57 bar |
| Component | Wt. % | Wt. % | Wt. % |
| MPG and other light compounds | 0.1 | 2.0 | 0.0 |
| 1,2-BDO | 2.5 | 32.4 | 0.1 |
| MEG | 97.4 | 65.6 | 99.9 |
| Heavier compounds | 0.0 | 0.0 | 0.0 |

TABLE 2

MEG/1,2-BDO Ratio of 20; 95% MEG Recovery

|  | Feed | Top | Bottom |
|---|---|---|---|
| Temperature | 170° C. | 175° C. | 180° C. |
| Pressure | 0.6 Bar | 0.5 Bar | 0.57 bar |
| Component | Wt. % | Wt. % | Wt. % |
| MPG and other light compounds | 0.1 | 1.5 | 0.0 |
| 1,2-BDO | 4.8 | 49.2 | 0.1 |
| MEG | 95.0 | 49.3 | 99.9 |
| Heavier compounds | 0.0 | 0.0 | 0.0 |

TABLE 3

MEG/1,2-BDO Ratio of 10; 95% MEG Recovery

|  | Feed | Top | Bottom |
|---|---|---|---|
| Temperature | 170° C. | 175° C. | 180° C. |
| Pressure | 0.6 Bar | 0.5 Bar | 0.57 bar |
| Component | Wt. % | Wt. % | Wt. % |
| MPG and other light compounds | 0.1 | 0.7 | 0.0 |
| 1,2-BDO | 9.1 | 49.7 | 0.1 |
| MEG | 90.7 | 49.6 | 99.9 |
| Heavier compounds | 0.0 | 0.0 | 0.0 |

TABLE 4

MEG/1,2-BDO Ratio of 10; 90% MEG Recovery

|  | Feed | Top | Bottom |
|---|---|---|---|
| Temperature | 170° C. | 174° C. | 180° C. |
| Pressure | 0.6 Bar | 0.5 Bar | 0.57 bar |
| Component | Wt. % | Wt. % | Wt. % |
| MPG and other light compounds | 0.1 | 0.7 | 0.0 |
| 1,2-BDO | 9.1 | 49.7 | 0.1 |
| MEG | 90.7 | 49.6 | 99.9 |
| Heavier compounds | 0.0 | 0.0 | 0.0 |

TABLE 5

MEG/1,2-BDO Ratio of 80; 99% MEG Recovery

|  | Feed | Top | Bottom |
|---|---|---|---|
| Temperature | 170° C. | 175° C. | 180° C. |
| Pressure | 0.6 Bar | 0.5 Bar | 0.57 bar |
| Component | Wt. % | Wt. % | Wt. % |
| MPG and other light compounds | 0.1 | 6.4 | 0.0 |
| 1,2-BDO | 1.2 | 51.1 | 0.1 |
| MEG | 98.6 | 42.5 | 99.9 |
| Heavier compounds | 0.0 | 0.0 | 0.0 |

TABLE 6

MEG/1,2-BDO Ratio of 40; 95% MEG Recovery; Heavies Present in the Feed; 1,2-BDO Separation Column

|  | Feed | Top | Bottom |
|---|---|---|---|
| Temperature | 170° C. | 180° C. | 185° C. |
| Pressure | 0.6 Bar | 0.625 Bar | 0.688 bar |
| Component | Wt. % | Wt. % | Wt. % |
| MPG and other light compounds | 0.1 | 2.0 | 0.1 |
| 1,2-BDO | 2.4 | 32.5 | 0.0 |
| MEG | 95.4 | 65.5 | 97.8 |
| Heavier compounds | 2.0 | 0.0 | 2.1 |

TABLE 7

Heavies Removal Column; MEG as Top Product

|  | Feed | Top | Bottom |
|---|---|---|---|
| Temperature | 185° C. | 175° C. | 202° C. |
| Pressure | 0.688 bar | 0.5 Bar | 0.57 bar |
| Component | Wt. % | Wt. % | Wt. % |
| MPG and other light compounds | 0.1 | 0.0 | 0.0 |
| 1,2-BDO | 0.0 | 0.0 | 0.0 |
| MEG | 97.8 | 99.9 | 18.6 |
| Heavier compounds | 2.1 | 0.1 | 81.4 |

Figure 4:
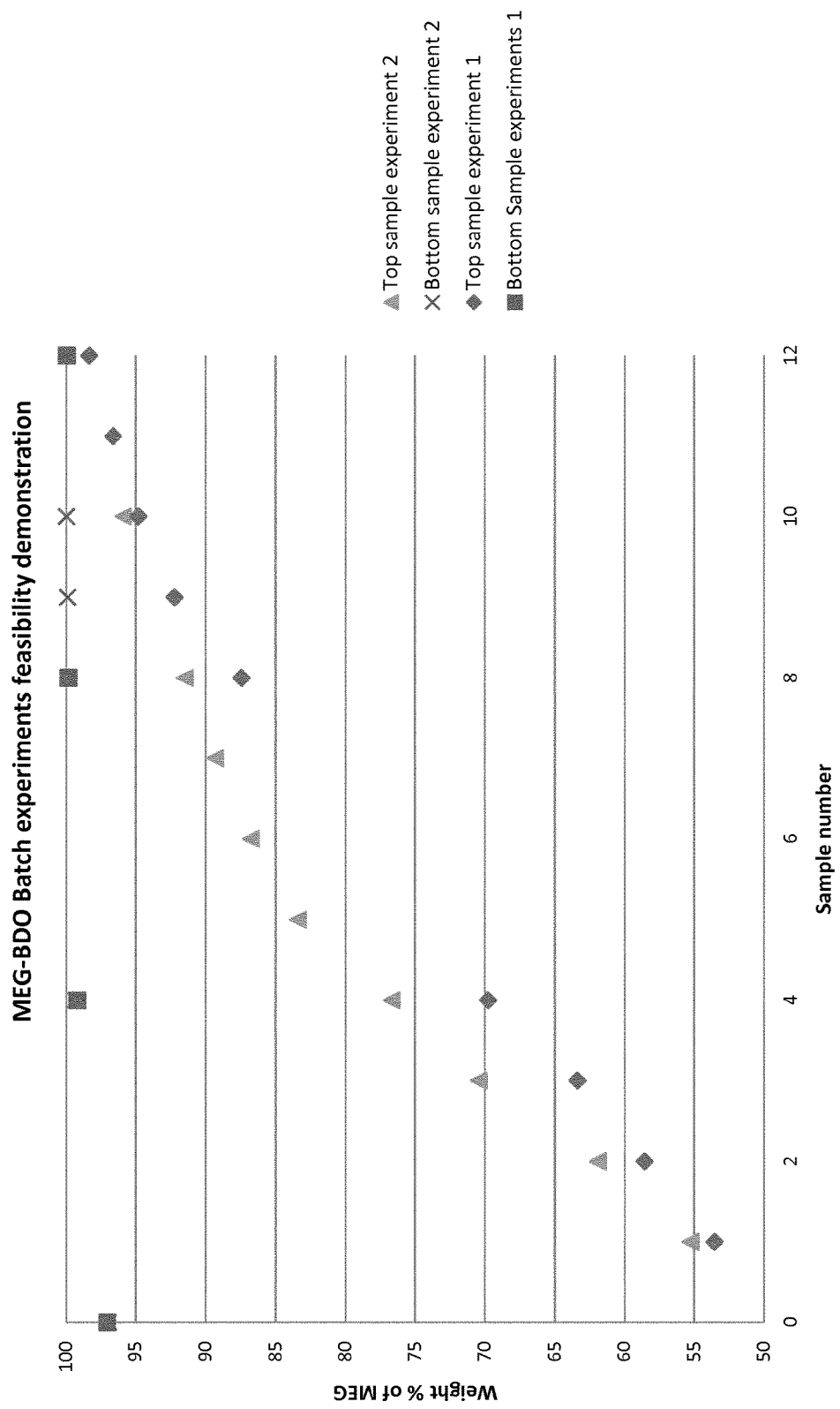
FIG. 4 is a graph showing the results of the Examples contained herein.

FIG. 4 shows with the results of two batch distillation experiments to demonstrate the concept feasibility for the separation of 1,2-BDO and MEG using a column with 30 trays. Each experiment was carried out at atmospheric pressure and with an infinite reflux ratio when not sampling and a reflux ratio of 5 when sampling. The initial mixture provided in each case was 97 wt % MEG, with the rest being BDO. A MEG-BDO mixture, at close to the azeotropic composition was obtained at the top of the column. Over time, the mixture was enriched in MEG as the MEG-BDO mixture was withdrawn with the top samples. Bottom samples were also taken to obtain the bottom composition profile. As can be seen, the result of the two experiments matched.

That which is claimed is:

1. A process for the separation of monoethylene glycol (MEG) and 1,2-butanediol (1,2-BDO) from a first mixture comprising MEG and 1,2-BDO in a weight ratio of at least 10:1 (MEG:1,2-BDO), said process comprising the steps of;
    (i) providing the first mixture as a feed to a distillation column at a point in the range of from 20 to 80% of the column height;
    (ii) operating the distillation at a temperature in the range of from 120 to 190° C. and at a pressure in the range of from 5 kPa to atmospheric pressure;
    (iii) removing an MEG stream from the distillation column at a point below the point at which the first mixture is fed;
    (iv) removing an overheads stream comprising an azeotrope of MEG and 1,2-BDO.

2. The process according to claim 1, wherein first mixture comprises MEG and 1,2-BDO in a weight ratio of at least 30:1.

3. The process according to claim 1, wherein the first mixture comprising MEG and 1,2-BDO is derived from the reaction product stream from a process for the hydrogenolysis of a saccharide or sugar alcohol containing feedstock.

4. The process according to claim 1, wherein the MEG stream comprises at least 95 wt % of the MEG present in the first mixture comprising MEG and 1,2-BDO.

5. The process according to claim 1, wherein the overheads stream contains in the range of from 30 to 55 wt % MEG.

6. The process according to claim 1, wherein the MEG stream is removed from the distillation column as a bottoms stream.

7. The process according to claim 1, wherein the MEG stream is removed from the distillation column at a point below the point at which the first mixture is fed and above the bottoms stream.

8. The process according to claim 1, wherein the overheads stream comprising an azeotrope of MEG and 1,2-BDO is subjected to further process steps in order to recover the MEG.

* * * * *